(12) United States Patent
Miyata

(10) Patent No.: US 11,906,374 B2
(45) Date of Patent: Feb. 20, 2024

(54) MEASUREMENT METHOD AND MEASUREMENT APPARATUS

(71) Applicant: YAMAHA Corporation, Hamamatsu (JP)

(72) Inventor: Tomoya Miyata, Hamamatsu (JP)

(73) Assignee: YAMAHA Corporation, Shizuoka (JP)

(*) Notice: Subject to any disclaimer, the term of this patent is extended or adjusted under 35 U.S.C. 154(b) by 601 days.

(21) Appl. No.: 17/015,302

(22) PCT Filed: Feb. 6, 2019

(86) PCT No.: PCT/JP2019/004244
§ 371 (c)(1),
(2) Date: Sep. 9, 2020

(87) PCT Pub. No.: WO2019/171865
PCT Pub. Date: Sep. 12, 2019

(65) Prior Publication Data
US 2021/0199517 A1    Jul. 1, 2021

(30) Foreign Application Priority Data
Mar. 9, 2018 (JP) ................. 2018-043558

(51) Int. Cl.
*G01L 1/16* (2006.01)
*G01H 11/08* (2006.01)
*G01L 1/10* (2006.01)

(52) U.S. Cl.
CPC .............. *G01L 1/167* (2013.01); *G01H 11/08* (2013.01); *G01L 1/103* (2013.01)

(58) Field of Classification Search
CPC . G01L 1/167; G01L 1/103; G01L 1/10; G01L 1/16; G01H 11/08; A61B 5/02; A61B 5/11
See application file for complete search history.

(56) References Cited

U.S. PATENT DOCUMENTS

| 4,546,658 A | 10/1985 | Rocha et al. |
| 2009/0199658 A1* | 8/2009 | Ando ............... G01L 1/162 73/862.59 |
| 2019/0025157 A1* | 1/2019 | Hebrard ............ F16C 19/52 |

FOREIGN PATENT DOCUMENTS

| CN | 1158077 C | 7/2004 |
| CN | 1320411 C | 6/2007 |
| JP | 07237484 A * | 9/1995 |
| JP | H07237484 A | 9/1995 |
| JP | 2000028444 A | 1/2000 |
| JP | 2000028445 A * | 1/2000 |

(Continued)

OTHER PUBLICATIONS

Notice of Reasons of Refusal in CN 201980017892.7 dated Apr 6, 2022.

(Continued)

*Primary Examiner* — Peter J Macchiarolo
*Assistant Examiner* — John M Royston
(74) *Attorney, Agent, or Firm* — CHIP LAW GROUP

(57) ABSTRACT

Provided is a measurement method including measuring, by using a piezoelectric sheet sensor in contact with a measurement object, vibration transmitted from the measurement object to the piezoelectric sheet sensor and measuring pressing force between the measurement object and the piezoelectric sheet sensor.

16 Claims, 3 Drawing Sheets

(56) References Cited

FOREIGN PATENT DOCUMENTS

| | | |
|---|---|---|
| JP | 2000028445 A | 1/2000 |
| JP | 2008183181 A | 8/2008 |
| JP | 4178600 B2 | 11/2008 |
| JP | 2015020015 A | 2/2015 |
| JP | 2015194445 A | 11/2015 |

OTHER PUBLICATIONS

Notice of Reasons of Refusal in CN 111837020 dated Jul. 15, 2021.
Notice of Reasons of Refusal in JP 2018-043558 dated Jun. 9, 2021.

* cited by examiner

MEASUREMENT METHOD AND MEASUREMENT APPARATUS

CROSS REFERENCE TO RELATED APPLICATIONS

This application is a continuation of International Patent Application No. PCT/JP2019/004244 filed Feb. 6, 2019, which claims the benefit of Japanese Priority Patent Application JP 2018-043558 filed Mar. 9, 2018. Each of the above-referenced applications is hereby incorporated herein by reference in its entirety.

BACKGROUND

The disclosure relates to a measurement method and a measurement apparatus that use a piezoelectric sheet sensor to measure vibration and pressing force.

Various apparatuses that measure pulse waves of living bodies, such as a human body, are provided. In this type of measurement apparatus, vibration, such as a pulse wave, is to be measured while the pressing force applied to the measurement object is maintained at an optimal value. To do so, it is needed that a function of measuring the pressing force to measuring object, in addition to a function of measuring the vibration, such as a pulse wave. An example of literature related to the technique of measuring a plurality of types of physical quantity includes Japanese Patent Laid-Open No. 2015-020015. In a sensor used in the technique described in Japanese Patent Laid-Open No. 2015-020015, a living body measurement sensor and an electrostatic sensor are laminated, and the living body measurement sensor starts the measurement when the change in the electrostatic capacity of the electrostatic sensor exceeds a threshold.

SUMMARY

In the sensor used in the technique in the related art, a vibration detection sensor and a press sensor are laminated. However, separate sensors including the vibration detection sensor and the press sensor arranged in the depth direction of the layer are to be prepared after all, and there is a problem that the cost of the measurement apparatus increases.

The disclosure has been made in view of the circumstances described above, and it is desirable to provide technical means for allowing measurement of both vibration transmitted from a measurement object and pressing force between a measurement apparatus and the measurement object without increasing the cost of the measurement apparatus.

The disclosure provides a measurement method including measuring, by using a piezoelectric sheet sensor in contact with a measurement object, vibration transmitted from the measurement object to the piezoelectric sheet sensor and measuring pressing force between the measurement object and the piezoelectric sheet sensor.

In addition, the disclosure provides a measurement apparatus including a piezoelectric sheet sensor that comes into contact with a measurement object and a measurement control unit that uses the piezoelectric sheet sensor to measure vibration transmitted from the measurement object to the piezoelectric sheet sensor and pressing force between the measurement object and the piezoelectric sheet sensor.

Further, the disclosure provides a piezoelectric sheet sensor including a vibration measurement electrode and a pressing force measurement electrode arranged on a common sheet-like piezoelectric body.

DETAILED DESCRIPTION OF THE PREFERRED EMBODIMENTS

Embodiments of the disclosure will now be described with reference to the drawings.

First Embodiment

Figure 1:
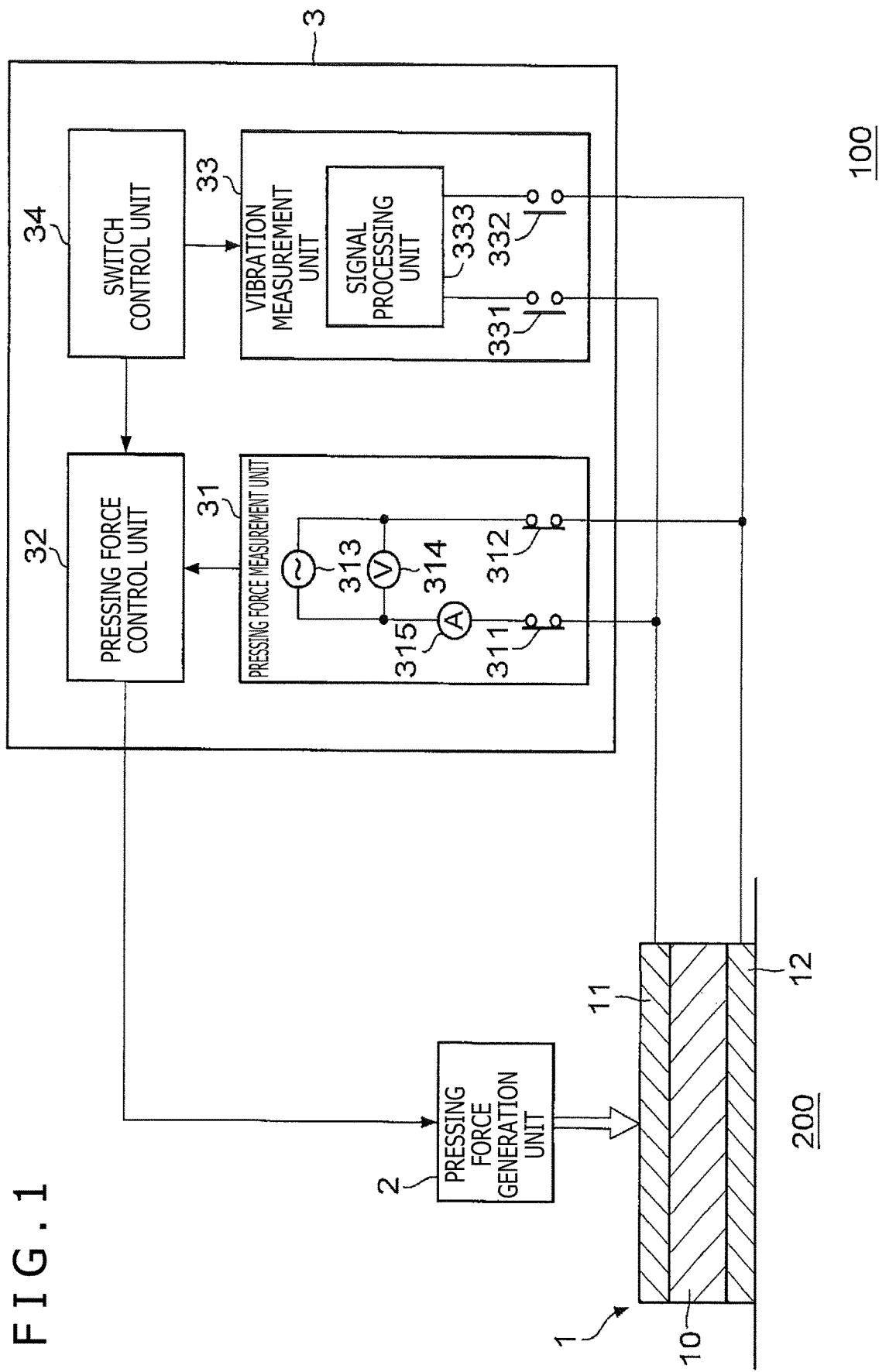
FIG. 1 is a block diagram illustrating a configuration of a measurement apparatus as a first embodiment of the disclosure.

FIG. 1 depicts a configuration of a measurement apparatus 100 as a first embodiment of the disclosure. The measurement apparatus 100 is an apparatus that measures pressing force applied to a measurement object 200 and vibration generated in the measurement object 200.

In the measurement apparatus 100, a piezoelectric sheet sensor 1 is pasted on the surface of the measurement object 200. A pressing force generation unit 2 is an apparatus that generates pressing force between the measurement object 200 and the piezoelectric sheet sensor 1, specifically, an apparatus that presses the piezoelectric sheet sensor 1 against the measurement object 200. The measurement object 200 in the present embodiment is a living body, specifically, a skin surface near an artery of a human body. In the present embodiment, the piezoelectric sheet sensor 1 is pressed against the skin surface of the human body with appropriate pressing force, and the piezoelectric sheet sensor 1 measures a vibration waveform from the artery, that is, a pulse waveform. A measurement control unit 3 is an apparatus including a function of using the piezoelectric sheet sensor 1 to measure the vibration generated in the measurement object 200, a function of measuring the pressing force applied from the pressing force generation unit 2 to the measurement object 200 through the piezoelectric sheet sensor 1, that is, the pressing force between the measurement object 200 and the piezoelectric sheet sensor 1, and a function of controlling the pressing force generated by the pressing force generation unit 2.

The piezoelectric sheet sensor 1 includes electrodes 11 and 12 pasted on both surfaces of a sheet-like piezoelectric body 10.

The sheet-like piezoelectric body 10 is formed by a piezoelectric material that converts pressure into voltage. The sheet-like piezoelectric body 10 is subject to stress due to the vibration and the pressing force (pressing force against the pressing force from the pressing force generation unit 2) from the measurement object 200, and a potential difference occurs according to the acceleration of the change in stress.

Although the piezoelectric material forming the sheet-like piezoelectric body 10 may be an inorganic material, such as lead zirconate titanate, it is preferable that the piezoelectric material be a flexible polymeric piezoelectric material that allows the sheet-like piezoelectric body 10 to be in close contact with the surface of the living body. Examples of the polymeric piezoelectric material include polyvinylidene fluoride (PVDF), vinylidene fluoride-trifluoroethylene copolymer (P(VDF/TrFE)), and vinylidene cyanide-vinyl acetate copolymer (P(VDCN/VAc)).

The sheet-like piezoelectric body 10 may also be provided by forming a large number of flat pores in, for example, polytetrafluoroethylene (PTFE), polypropylene (PP), polyethylene (PE), or polyethylene terephthalate (PET) without piezoelectric property, and the piezoelectric property may be provided by using, for example, corona discharge to polarize and charge the opposing surface of the flat pores.

The lower limit of the average thickness of the sheet-like piezoelectric body 10 is preferably 10 μm, more preferably, 50 μm. On the other hand, the upper limit of the average thickness of the sheet-like piezoelectric body 10 is preferably 500 μm, more preferably, 200 μm. The strength of the sheet-like piezoelectric body 10 may be insufficient when the average thickness of the sheet-like piezoelectric body 10 is less than the lower limit. On the other hand, when the average thickness of the sheet-like piezoelectric body 10 exceeds the upper limit, the deformability of the sheet-like piezoelectric body 10 may be small, and the detection sensitivity may be insufficient.

The electrodes 11 and 12 are laminated on both surfaces of the sheet-like piezoelectric body 10 and are used to detect the potential difference between the front and the back of the sheet-like piezoelectric body 10. That is, the electrode 11 (example of first electrode) is arranged on an upper surface (example of first surface) of the sheet-like piezoelectric body 10, and the electrode 12 (example of second electrode) is arranged on a lower surface (example of second surface) of the sheet-like piezoelectric body 10. The material of the electrodes 11 and 12 may be any conductive material, and examples of the material include metal, such as aluminum, copper, and nickel, and carbon.

The average thickness of the electrodes 11 and 12 is not particularly limited, and the average thickness can, for example, be 0.1 to 30 μm depending on the lamination method. The strength of the electrodes 11 and 12 may be insufficient when the average thickness of the electrodes 11 and 12 is less than the lower limit. On the other hand, the transmission of vibration to the sheet-like piezoelectric body 10 may be inhibited when the average thickness of the electrodes 11 and 12 exceeds the upper limit.

The method of laminating the electrodes 11 and 12 on the sheet-like piezoelectric body 10 is not particularly limited, and examples of the lamination method include deposition of metal, printing of carbon conductive ink, and application and drying of silver paste.

The measurement control unit 3 includes a pressing force measurement unit 31, a pressing force control unit 32, a vibration measurement unit 33, and a switch control unit 34.

The pressing force measurement unit 31 is an apparatus that measures the pressing force applied from the pressing force generation unit 2 to the measurement object 200 through the piezoelectric sheet sensor 1, that is, the pressing force between the measurement object 200 and the piezoelectric sheet sensor 1. The pressing force measurement unit 31 includes switches 311 and 312, an alternating current (AC) power supply 313, a voltage measurement unit 314, and a current measurement unit 315. In the pressing force measurement unit 31, the switches 311 and 312 are turned on to apply an output voltage of the AC power supply 313 to the electrodes 11 and 12 of the piezoelectric sheet sensor 1 through the current measurement unit 315. In this state, an AC voltage is applied from the AC power supply 313, and the pressing force measurement unit 31 acquires a signal indicating a change in the resonance frequency of the piezoelectric sheet sensor 1. The pressing force measurement unit 31 measures the pressing force between the measurement object 200 and the piezoelectric sheet sensor 1 based on the acquired signal.

There can be various modes regarding the process of measuring the pressing force. In a first mode, a frequency variable AC power supply is used as the AC power supply 313, and the current measurement unit 315 measures the current flowing through the piezoelectric sheet sensor 1 while the frequency of the AC voltage output by the AC power supply 313 is swept. The resonance frequency where the current flowing through the piezoelectric sheet sensor 1 is at the peak is detected, and the pressing force is obtained based on the dependence of the resonance frequency on the pressing force obtained in advance and based on the detected resonance frequency.

In a second mode, frequency transfer characteristics of the piezoelectric sheet sensor 1, that is, frequency characteristics of the impedance of the piezoelectric sheet sensor 1, are obtained for various levels of pressing force. The impedance of the piezoelectric sheet sensor 1 at a predetermined frequency is obtained based on measurement results of the voltage measurement unit 314 and the current measurement unit 315, and the pressing force is obtained based on the results and the frequency transfer characteristics corresponding to various levels of pressing force.

The pressing force control unit 32 is an apparatus that causes the pressing force measurement unit 31 to measure the pressing force and that converges the pressing force to an optimal value by increasing the pressing force if the result of the measurement is smaller than the optimal value and decreasing the pressing force if the result of the measurement is larger than the optimal value.

The vibration measurement unit 33 is an apparatus that measures vibration transmitted from the measurement object 200 to the piezoelectric sheet sensor 1. The vibration measurement unit 33 includes switches 331 and 332 and a signal processing unit 333. The signal processing unit 333 is connected to the electrodes 11 and 12 of the piezoelectric sheet sensor 1 when the switches 331 and 332 are turned on. The signal processing unit 333 includes a filter that passes a signal after selecting the signal belonging to the frequency band of the vibration wave to be measured from among the signals generated between the electrodes 11 and 12. In the present embodiment, the measurement object of the vibration measurement unit 33 is a pulse wave, and the frequency band of the pulse wave is lower than the resonance frequency of the piezoelectric sheet sensor 1. The filter passes a signal after selecting the signal in the low frequency band from among the signals between the electrodes 11 and 12 of the piezoelectric sheet sensor 1. The signal processing unit 333 displays the signal passing through the filter on an unillustrated display or analyzes parameters, such as amplitude and frequency of the signal, and notifies the user of the parameters.

The switch control unit 34 is a unit configured to alternately cause the pressing force control unit 32 to control the measurement of the pressing force and the adjustment of the pressing force and cause the vibration measurement unit 33 to measure the vibration. That is, the switch control unit 34 prevents each of a period for the measurement of the pressing force (example of first period) and a period for the adjustment of the pressing force performed by the pressing force control unit 32 from overlapping a period for the measurement of the vibration (example of second period) performed by the vibration measurement unit 33. Specifically, the switch control unit 34 controls the switches 311, 312, 331, and 332 to prevent the period in which the switches 311 and 312 are turned on and the period in which the switches 331 and 332 are turned on from overlapping each other.

Figure 2:
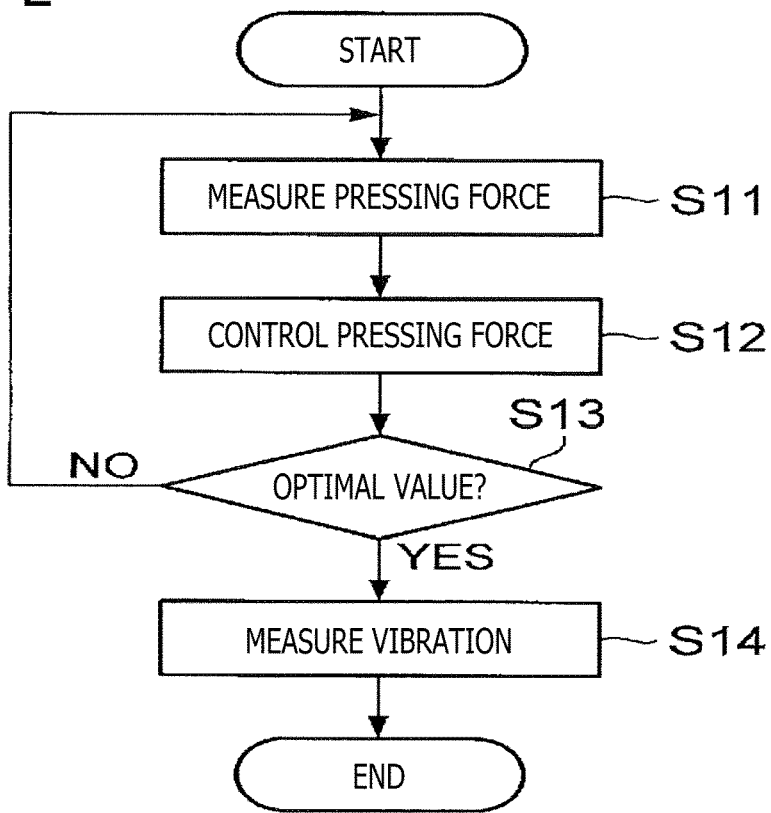
FIG. 2 is a flowchart illustrating a first example of operation of the embodiment.

FIG. 2 is a flowchart illustrating a first example of operation of the present embodiment. In the example, the switch control unit 34 of the measurement control unit 3 turns on the switches 311 and 312 and turns off the switches 331 and 332. The switch control unit 34 sequentially causes the pressing force measurement unit 31 to measure the pressing force using the piezoelectric sheet sensor 1 (step S11) and causes the pressing force control unit 32 to control the pressing force, specifically, to control the pressing force to bring the pressing force close to the optimal value (step S12). The switch control unit 34 determines whether or not the pressing force has converged to the optimal value (example of preset predetermined magnitude) (step S13). The switch control unit 34 repeats steps S11 to S13 if the pressing force has not converged to the optimal value.

Once the pressing force is converged to the optimal value so that the determination result of step S13 is "YES," the switch control unit 34 turns off the switches 311 and 312 and turns on the switches 331 and 332. The switch control unit 34 causes the vibration measurement unit 33 to measure the vibration using the piezoelectric sheet sensor 1 (step S14) and ends the process. That is, the measurement control unit 3 turns off the switches 311 and 312 to end the measurement and the adjustment of the pressing force and turns on the switches 331 and 332 to start the measurement of the vibration.

The first example of operation is useful when the vibration of the measurement object 200 is to be measured only once at the optimal pressing force.

Figure 3:
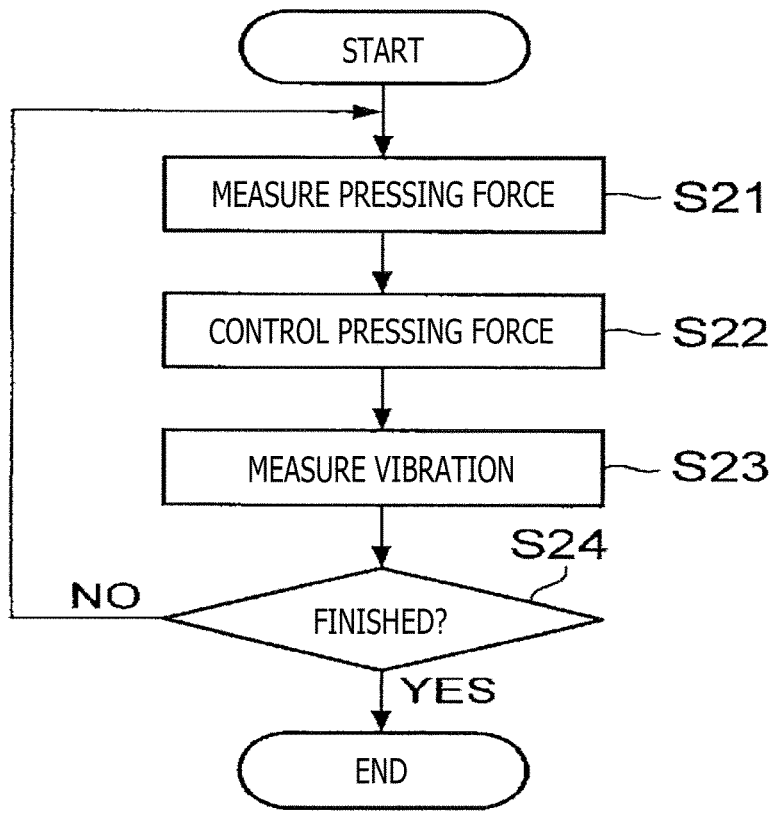
FIG. 3 is a flowchart illustrating a second example of operation of the embodiment.

FIG. 3 is a flowchart illustrating a second example of operation of the present embodiment. In the example, the switch control unit 34 of the measurement control unit 3 turns on the switches 311 and 312 and turns off the switches 331 and 332. The switch control unit 34 sequentially causes the pressing force measurement unit 31 to measure the pressing force using the piezoelectric sheet sensor 1 (step S21) and causes the pressing force control unit 32 to control the pressing force, specifically, to control the pressing force to bring the pressing force close to the optimal value (step S22). The switch control unit 34 then turns off the switches 311 and 312 and turns on the switches 331 and 332. The switch control unit 34 causes the vibration measurement unit 33 to measure the vibration using the piezoelectric sheet sensor 1 (step S23). The switch control unit 34 then determines whether or not an unillustrated operator is operated to give instructions on end of the measurement. The switch control unit 34 repeats steps S21 to S24 if the determination result is "NO" and ends the process if the determination result is "YES."

The second example of operation is useful when the measurement of the vibration of the measurement object 200 is repeated for a long period of time while the pressing force is maintained at the optimal value.

In this way, according to the present embodiment, one piezoelectric sheet sensor 1 can measure both the pressing force and the vibration. That is, electrodes functioning as a vibration measurement electrode and a pressing force measurement electrode are arranged on a common sheet-like piezoelectric body, and the pressing force and the vibration can be measured inexpensively.

Second Embodiment

Figure 4:
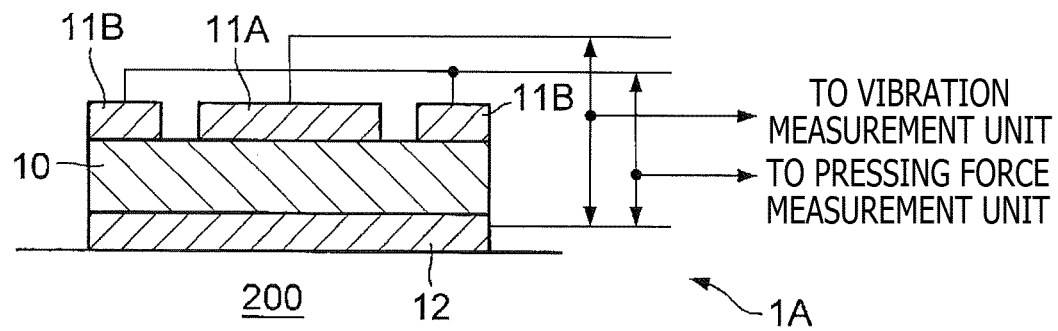
FIG. 4 is a cross-sectional view illustrating a configuration of a piezoelectric sheet sensor used in a measurement apparatus as a second embodiment of the disclosure.

FIG. 4 is a cross-sectional view illustrating a configuration of a piezoelectric sheet sensor 1A used in a measurement apparatus as a second embodiment of the disclosure. In the piezoelectric sheet sensor 1A, the electrode 11 of the piezoelectric sheet sensor 1 in the first embodiment is replaced with a vibration measurement electrode 11A and a pressing force measurement electrode 11B electrically separated from each other. In the present embodiment, the vibration measurement electrode 11A and the electrode 12 are connected to the vibration measurement unit 33 of the first embodiment, and the pressing force measurement electrode 11B and the electrode 12 are connected to the pressing force measurement unit 31 of the first embodiment.

An advantageous effect similar to that of the first embodiment can also be obtained in the present embodiment. In addition, the vibration measurement electrode 11A and the pressing force measurement electrode 11B are electrically separated in the present embodiment. This allows the measurement of the pressing force performed by application of the AC voltage between the pressing force measurement electrode 11B and the electrode 12 and the measurement of the vibration performed by measurement of the voltage between the vibration measurement electrode 11A and the electrode 12 to be performed simultaneously. That is, the period for measuring the vibration at least partially overlaps the period for measuring the pressing force. This is advantageous in that the measurement of the pressing force and the measurement of the vibration can easily be controlled. In addition, the vibration measurement electrode and the pressing force measurement electrode are arranged on the common sheet-like piezoelectric body. Therefore, the pressing force and the vibration can be measured inexpensively.

Third Embodiment

Figure 5:
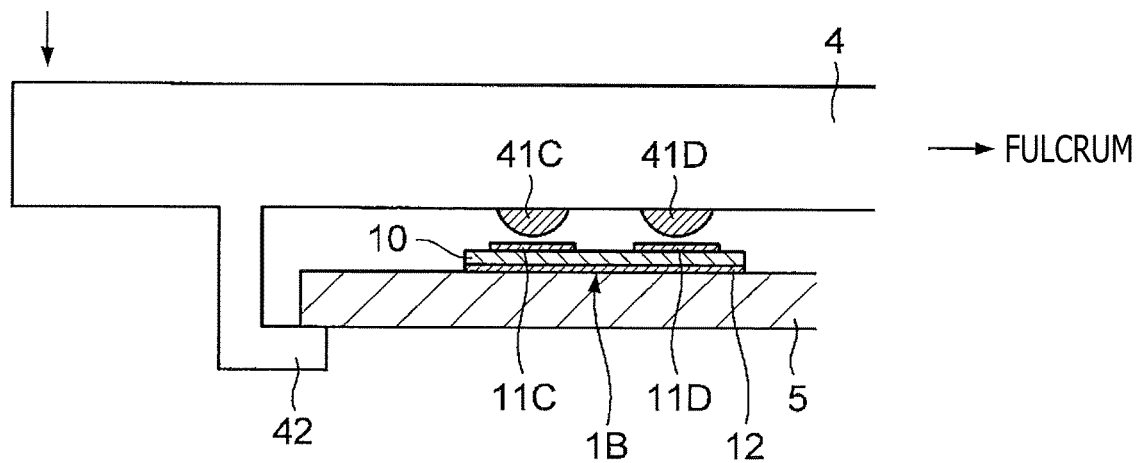
FIG. 5 depicts a configuration of a measurement apparatus as a third embodiment of the disclosure.

FIG. 5 is a cross-sectional view illustrating a configuration of a measurement apparatus as a third embodiment of the disclosure. The measurement apparatus of the present embodiment is a key press detection apparatus of a keyboard electronic musical instrument.

A general keyboard electronic musical instrument is provided with sensors that detect initial touches of key press operation and sensors that detect after-touches. Here, the sensors that detect the initial touches are provided for each of individual keys of the keyboard. However, as for the sensors that detect the after-touches, one sensor is generally provided in a high tone area among all of the keys in the keyboard, and another sensor is generally provided in a low tone area, in order to prevent an increase in the size and an increase in the cost of the keyboard.

The present embodiment allows detection of the initial touch and the after-touch in each of the individual keys of the keyboard without increasing the size and the cost of the keyboard.

In FIG. 5, a key 4 is supported by a fulcrum on the right side of the key 4 and is positioned above a base material 5. When the left edge of the key 4 is pressed by a finger of the player, the key 4 moves around the fulcrum and approaches the base material 5.

A piezoelectric sheet sensor 1B facing the back surface of the key 4 is arranged on the front surface of the base material 5. The piezoelectric sheet sensor 1B includes a vibration measurement electrode and a pressing force measurement electrode in a common sheet-like piezoelectric body similarly to the piezoelectric sheet sensor of the second embodiment. The electrode 12 pasted on the surface of the sheet-like piezoelectric body 10 closer to the base material 5 is fixed to the front surface of the base material 5. An initial touch measurement electrode 11C and an after-touch measurement electrode 11D are arranged in the longitudinal direction of the key 4, on the surface of the sheet-like piezoelectric body 10 closer to the key 4. Here, the initial touch measurement electrode 11C is positioned closer to the key press section in the key 4, compared to the after-touch measurement electrode 11D. Two projecting portions 41C and 41D rising toward the initial touch measurement electrode 11C and the after-touch measurement electrode 11D are provided on the back surface of the key 4.

In the piezoelectric sheet sensor 1B, the initial touch measurement electrode 11C and the electrode 12 are connected to an unillustrated initial touch detection circuit. The initial touch detection circuit is a circuit equivalent to the vibration measurement unit 33 of the first embodiment. In the piezoelectric sheet sensor 1B, the after-touch measurement electrode 11D and the electrode 12 are connected to an unillustrated after-touch detection circuit. The after-touch detection circuit is a circuit equivalent to the pressing force measurement unit 31 of the first embodiment. A hook-shaped stopper 42 is also formed from the key 4 such that the stopper 42 is in contact with the lower edge surface of the key press side of the base material 5. The stopper 42 prevents the key 4 from being warped upward more than necessary.

Once the key 4 is pressed in such a configuration, the projecting portions 41C and 41D on the back surface of the key 4 approach the base material 5 and collide with the initial touch measurement electrode 11C and the after-touch measurement electrode 11D, respectively. The initial touch detection circuit generates initial touch information indicating the key press speed, based on, for example, the rising speed of the voltage waveform between the electrodes 11C and 12. The after-touch detection circuit executes a process similar to that of the pressing force measurement unit 31 of the first embodiment to measure the pressing force applied from the key 4 side to the base material 5 through the piezoelectric sheet sensor 1B and generates after-touch information indicating the pressing force. The keyboard electronic musical instrument controls the formation of music based on the initial touch information and the after-touch information generated in such way.

As described above, the present embodiment can realize a small-sized low-cost keyboard electronic musical instrument having a function of detecting the initial touch and the after-touch in each of the individual keys included in the keyboard.

In the first and second embodiments, the measurement object 200 includes the blood vessel as a vibration source. On the other hand, the measurement objects in the present embodiment are two projecting portions 41C and 41D provided on the key 4. The key is pressed to bring the measurement object in contact with the piezoelectric sheet sensor 1B, and the vibration (specifically, shock wave) is transmitted from the measurement object to the piezoelectric sheet sensor 1B. The pressing force is generated between the measurement object and the piezoelectric sheet sensor 1B. In this way, the present disclosure is applied not only to the mode in which the measurement object includes the vibration source, but also to the mode in which the vibration is generated by the contact of the measurement object and the piezoelectric sheet sensor.

Other Embodiments

While the embodiments of the disclosure have been described above, there can also be other embodiments for the disclosure. For example, in the third embodiment, only the initial touch detection circuit is connected to the piezoelectric sheet sensor 1B before the key press, and the after-touch detection circuit is separated. When the key is pressed, the initial touch detection circuit generates the initial touch information, and then, the after-touch detection circuit is connected to the piezoelectric sheet sensor 1B only for a predetermined period of time to cause the after-touch detection circuit to generate the after-touch information. According to the mode, the after-touch detection circuit is separated from the piezoelectric sheet sensor 1B in the initial stage after the key press, and the initial touch detection circuit can thus obtain the voltage waveform accurately reflecting the key press speed from the piezoelectric sheet sensor 1B. The after-touch detection circuit is connected to the piezoelectric sheet sensor 1B after the initial touch detection circuit generates the initial touch information, and therefore, the after-touch detection circuit can generate the after-touch information reflecting the after-touch, that is, the pressing force applied to the key 4 after the end of the key press. In the third embodiment, the electrode that detects the vibration and the electrode that measures the press may be shared as in the first embodiment.

It should be understood by those skilled in the art that various modifications, combinations, sub-combinations and alterations may occur depending on design requirements and other factors insofar as they are within the scope of the appended claims or the equivalent thereof.

What is claimed is:

1. A measurement method, comprising:
    measuring, by using a piezoelectric sheet sensor in contact with a measurement object, vibration transmitted from the measurement object to the piezoelectric sheet sensor; and
    measuring a pressing force between the measurement object and the piezoelectric sheet sensor, wherein
        in the measuring of the pressing force, the pressing force between the measurement object and the piezoelectric sheet sensor is measured based on a signal generated between a pressing force measurement electrode arranged on a first surface of a sheet-like piezoelectric body and a second electrode arranged on a second surface of the sheet-like piezoelectric body,
        in the measuring of the vibration, the vibration transmitted from the measurement object to the piezoelectric sheet sensor is detected based on a signal generated between a vibration measurement electrode arranged on the first surface of the sheet-like piezoelectric body and the second electrode, and
        the pressing force measurement electrode is electrically separated from the vibration measurement electrode.

2. The measurement method according to claim 1, wherein a first period in which the vibration is measured in the measuring of the vibration is not overlapping a second period in which the pressing force is measured in the measuring of the pressing force.

3. The measurement method according to claim 1, further comprising determining whether a magnitude of the pressing force measured in the measuring of the pressing force is a predetermined magnitude, wherein, based on the determination that the magnitude of the pressing force measured is the predetermined magnitude, the measuring of the pressing force is finished, and the measuring of the vibration is started.

4. The measurement method according to claim 1, wherein,
in the measuring of the pressing force, the pressing force between the measurement object and the piezoelectric sheet sensor is measured based on a first signal generated between a first electrode arranged on the first surface of the sheet-like piezoelectric body and the second electrode arranged on the second surface of the sheet-like piezoelectric body, and
in the measuring of the vibration, the vibration transmitted from the measurement object to the piezoelectric sheet sensor is detected based on a second signal generated between the first electrode and the second electrode.

5. The measurement method according to claim 1, wherein a first period in which the vibration is measured in the measuring of the vibration at least partially overlaps a second period in which the pressing force is measured in the measuring of the pressing force.

6. The measurement method according to claim 1, further comprising controlling one or more switches, connected to the piezoelectric sheet sensor, to alternately perform the measurement of the vibration and the measurement of the pressing force.

7. The measurement method according to claim 1, further comprising:
adjusting the pressing force between the measurement object and the piezoelectric sheet sensor, based on the measured pressing force; and
measuring the vibration transmitted from the measurement object and the piezoelectric sheet sensor subsequent to the adjustment.

8. A measurement apparatus, comprising:
a piezoelectric sheet sensor configured to come into contact with a measurement object; and
a measurement control unit configured to use the piezoelectric sheet sensor to measure vibration transmitted from the measurement object to the piezoelectric sheet sensor and a pressing force between the measurement object and the piezoelectric sheet sensor, wherein
in the measurement of the pressing force, the pressing force between the measurement object and the piezoelectric sheet sensor is measured based on a signal generated between a pressing force measurement electrode arranged on a first surface of a sheet-like piezoelectric body and a second electrode arranged on a second surface of the sheet-like piezoelectric body,
in the measurement of the vibration, the vibration transmitted from the measurement object to the piezoelectric sheet sensor is detected based on a signal generated between a vibration measurement electrode arranged on the first surface of the sheet-like piezoelectric body and the second electrode, and
the pressing force measurement electrode is electrically separated from the vibration measurement electrode.

9. The measurement apparatus according to claim 8, wherein the measurement control unit is further configured to measure the pressing force in a first period and measure the vibration in a second period not overlapping the first period.

10. The measurement apparatus according to claim 9, wherein
the piezoelectric sheet sensor includes the sheet-like piezoelectric body, a first electrode arranged on the first surface of the sheet-like piezoelectric body, and the second electrode arranged on the second surface of the sheet-like piezoelectric body, and
the measurement control unit is further configured to apply an alternating current voltage between the first electrode and the second electrode to detect the pressing force.

11. The measurement apparatus according to claim 10, wherein the measurement control unit is further configured to:
measure the pressing force between the measurement object and the piezoelectric sheet sensor, based on a first signal generated between the first electrode and the second electrode; and
measure the vibration transmitted from the measurement object to the piezoelectric sheet sensor, based on a second signal generated between the first electrode and the second electrode.

12. The measurement apparatus according to claim 9, further comprising a switch control unit configured to control one or more switches to sequentially switch the measurement of the pressing force and the measurement of the vibration.

13. The measurement apparatus according to claim 8, wherein the measurement control unit is further configured to:
apply an alternating current signal to acquire a signal indicating a change in a resonance frequency of the piezoelectric sheet sensor; and
measure the pressing force between the measurement object and the piezoelectric sheet sensor, based on the acquired signal.

14. The measurement apparatus according to claim 8, further comprising a pressing force control unit configured to adjust the pressing force between the measurement object and the piezoelectric sheet sensor, based on the measured pressing force.

15. The measurement apparatus according to claim 8, further comprising a pressing force generation unit configured to generate the pressing force between the measurement object and the piezoelectric sheet sensor.

16. A piezoelectric sheet sensor, comprising:
a vibration measurement electrode and a pressing force measurement electrode arranged on a same side of a common sheet-like piezoelectric body, wherein
the vibration measurement electrode is electrically separated from the pressing force measurement electrode, and
a first period for measuring a vibration at least partially overlaps a second period for measuring pressing force.

* * * * *